United States Patent [19]

Schneider et al.

[11] Patent Number: 4,610,676
[45] Date of Patent: Sep. 9, 1986

[54] OSTOMY APPLIANCE COUPLING RING CONSTRUCTION

[75] Inventors: Barry L. Schneider, Deerfield; Marvin E. Jensen, Niles; Mahmood Mohiuddin, Lake Zurich, all of Ill.

[73] Assignee: Hollister Incorporated, Libertyville, Ill.

[21] Appl. No.: 611,423

[22] Filed: May 17, 1984

[51] Int. Cl.[4] ............................................. A61F 5/44
[52] U.S. Cl. .................................................. 604/339
[58] Field of Search ............................... 604/332–344

[56] References Cited

U.S. PATENT DOCUMENTS 3,528,420 9/1970 Nielsen ................................ 128/283

FOREIGN PATENT DOCUMENTS 1105558 4/1961 Fed. Rep. of Germany ...... 604/338
1455784 11/1976 United Kingdom ................ 604/337

Primary Examiner—Ferris H. Lander
Attorney, Agent, or Firm—Tilton, Fallon, Lungmus

[57] ABSTRACT

A coupling for an ostomy appliance that detachably joins an ostomy bag to a faceplate capable of being adhesively secured to a patient's skin about a stoma opening. Each coupling ring is formed of flexible and resilient thermoplastic material, with one of the rings having an axially-extending frusto-conical neck portion and the other ring having a frusto-conical collar portion detachably receiving and sealingly engaging the neck portion. Primary latching is achieved in an annular zone spaced a substantial distance radially outwardly from the area of sealing engagement between the neck and collar portions, such latching action being provided by a shoulder extending about the outer periphery of one of the rings and a latching rib, defining a shoulder-receiving recess, extending about the outer periphery of the other ring.

21 Claims, 9 Drawing Figures

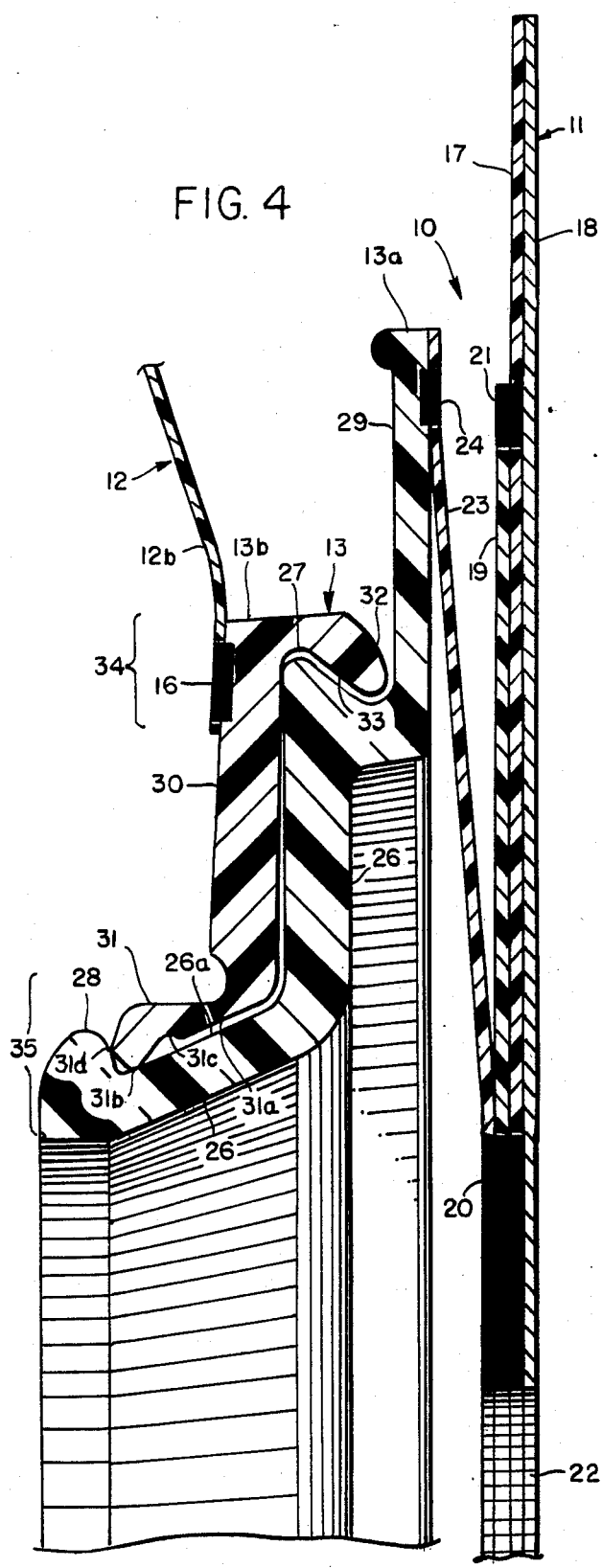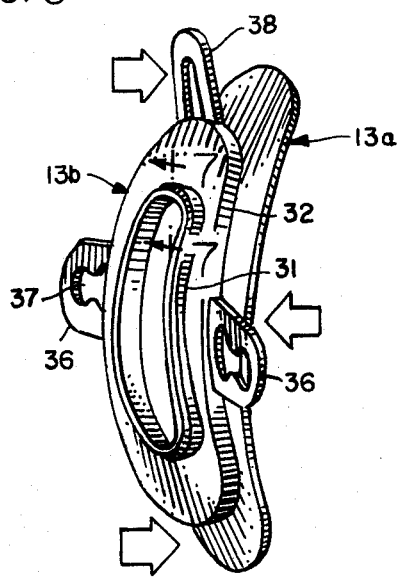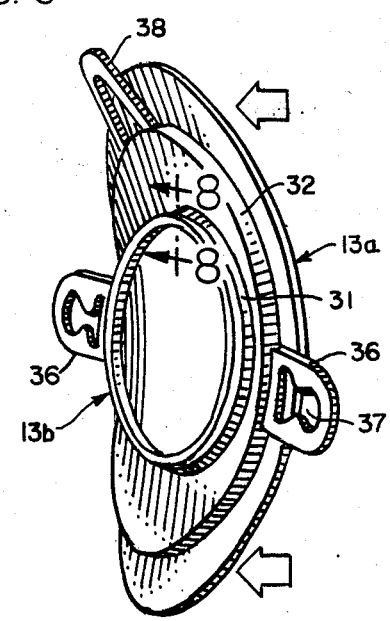

OSTOMY APPLIANCE COUPLING RING CONSTRUCTION

BACKGROUND AND SUMMARY

U.S. Pat. No. 3,528,420 discloses a coupling for ostomy appliances which takes the form of a pair of hard but nevertheless deformable plastic rings having generally frusto-conical sealing surfaces, one of the rings 20 being secured to a faceplate 16 and the other ring 14 being attached to ostomy bag 10. A lock flange 26 on the inner ring is intended to provide an abutment for the outer ring to lock or latch the rings together until separation is desired.

The latching system disclosed in that patent has not achieved notable commercial success and, although the reasons for such lack of success may be various, applicants have found that such an arrangement may be prone to unintentional detachment of the rings under conditions of use. Some deformability of the rings is necessary in order to permit intentional coupling and uncoupling; however, too much deformability may give rise to unintentional uncoupling of the rings in response to body movements of the wearer. The rings, especially faceplate ring 20, must therefore be relatively stiff, but such stiffness is also objectionable because body contact with a rigid ring may be expected to result in wearer discomfort.

One aspect of the present invention lies in the discovery that the system disclosed in the aforementioned patent may be the basis for a highly effective ostomy appliance coupling if the primary latching function is displaced radially outwardly and is performed by structure not indicated in that patent. With the essential function of the frusto-conical ring assembly of the patent limited to sealing rather than latching, and with the primary latching zone being located outwardly from the sealing zone, it has been found that the rings may be formed of a relatively soft plastic material (such as polyethylene) having substantial yieldability without risk that deformation might result in unintentional separation of the parts. The result is a ring assembly that has sufficient deformability for wearer comfort but still provides secure attachment and sealing effectiveness despite ring distortions arising from body movement. Intentional coupling and uncoupling may be readily achieved without direct contact with the stoma because the bag ring is disposed externally (radially outwardly) of the faceplate ring. Since the primary latching action occurs well outboard from the sealing zone, the result is a relatively flat ring assembly in which the radial width of each ring may be substantially greater than its axial depth.

In brief, the coupling ring construction of this invention takes the form of first and second coupling rings composed of flexible, resilient, thermoplastic material, the first ring having an annular body portion merging along its inner perimeter with a tubular neck portion that extends axially away from that body portion. The neck portion has a frusto-conical outer surface and has a free end terminating in an annular and radially-outwardly projecting rim.

The second ring also has an annular body portion and, in addition, an inner collar portion for detachably receiving the neck portion of the first ring. Unlike prior constructions, the annular body portions of both the first and second rings are generally planar with the body portion of the first ring having a latching shoulder extending about its outer perimeter and with the body portion of the second ring having an outer annular latching rib projecting inwardly and axially in a generally axial direction opposite from the direction of the collar portion. The latching rib, along with the remainder of the body portion of the second ring, defines an outer latching recess for detachably receiving and retaining the shoulder of the first ring.

The radial spacing between the latching and sealing functions promotes security of attachment even under severe conditions of use when the deformity of the rings is great enough to alter the areas of contact between the sealing surfaces. Under such circumstances, it has been found that since the parts continue to be held together by the primary latching action, normal sealing contact along the inner sealing zone is retained or restored when the deforming forces are removed.

Other features, advantages, and objects of the invention will become apparent from the specification and drawings.

DRAWINGS

FIG. 4 is a greatly enlarged fragmentary sectional view showing the primary latching and sealing zones of the coupling ring assembly.

FIG. 5 is a perspective view showing the coupled rings deformed in one direction as might occur during use (the bag and faceplate being omitted and the deformation being somewhat exaggerated for illustrative purposes).

FIG. 6 is a perspective view showing the coupling ring assembly deformed in another direction, the deformation again being exaggerated for illustrative purposes.

DETAILED DESCRIPTION OF PREFERRED EMBODIMENTS

Figure 1:
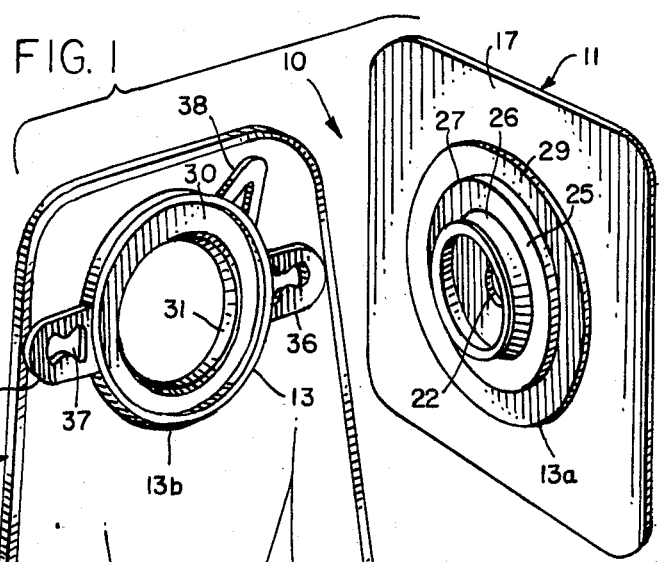
FIG. 1 is a perspective view of an ostomy appliance equipped with the coupling ring assembly of this invention, the ostomy bag and faceplate being shown in separated condition for clarity of illustration.
Figure 2:
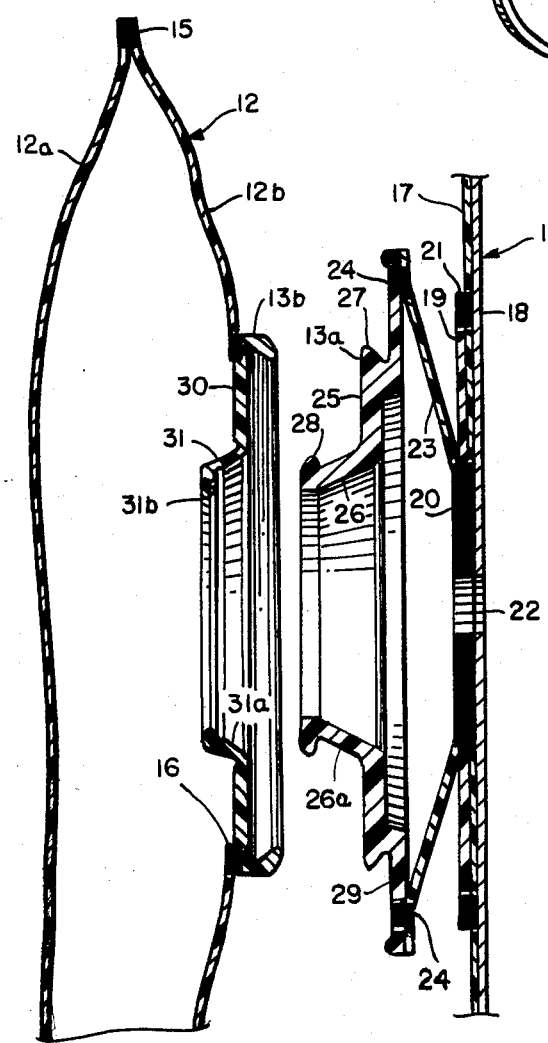
FIG. 2 is an enlarged fragmentary sectional view showing the coupling ring assembly in disconnected condition.
Figure 3:
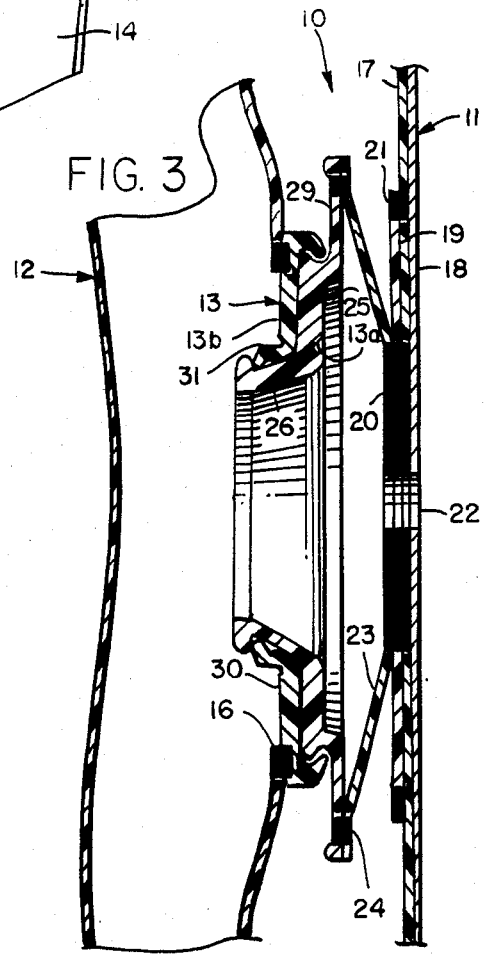
FIG. 3 is a sectional view similar to FIG. 2 but showing the rings in coupled condition.
Figure 7:
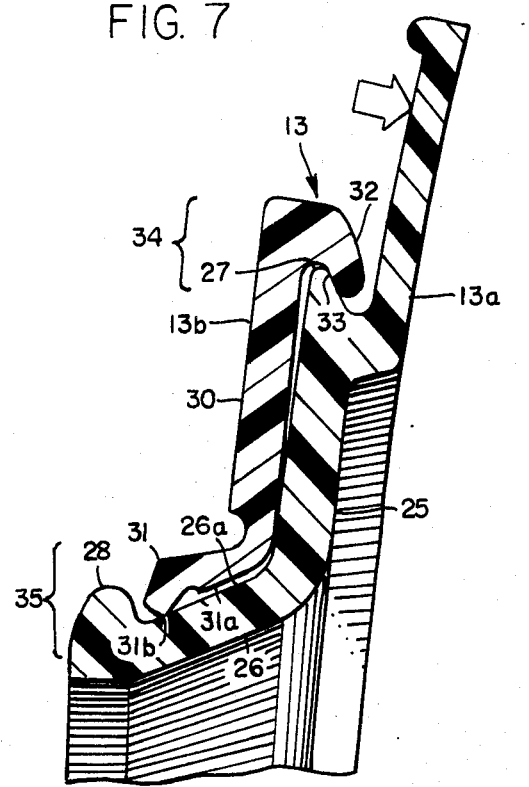
FIG. 7 is a greatly enlarged and somewhat schematic sectional view taken along line 7—7 of FIG. 5.
Figure 8:
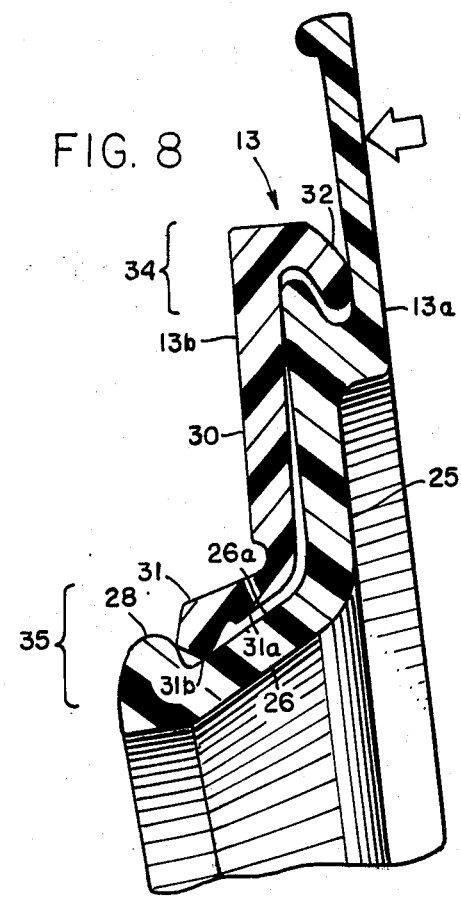
FIG. 8 is a greatly enlarged and somewhat schematic sectional view taken along line 8—8 of FIG. 6.

Referring to FIGS. 1-3, the numeral 10 generally designates an ostomy appliance having a faceplate 11 and a bag or pouch 12. A two-piece coupling ring assembly 13 is provided for detachably coupling the faceplate and pouch, one element of the assembly being faceplate ring 13a and the other being pouch ring 13b.

Both the pouch and faceplate may vary considerably in size, shape, and construction, all as well known in the art, and it is to be understood that coupling assembly 13 is not limited in its use to the particular pouch and faceplate constructions depicted in the drawings. For example, pouch 12 is shown to have an outlet 14 at its lower end, such outlet being intended to be closed by a suitable clamping device (not shown) such as the one disclosed in U.S. Pat. No. 3,523,534; however, the pouch may if desired be "non-drainable," in which case outlet 14 would be omitted. Typically, pouch 12 is designed to be relatively flat and is composed of two sheets or walls 12a and 12b of flexible thermoplastic film that are heat sealed together along their outer margins as indicated at 15 in the drawings. One wall 12b, which may be regarded as the rear wall that would face the abdomen of the patient when the appliance is worn, is provided near at its upper end with an opening 16 (FIGS. 2, 3).

Faceplate 11, in the particular form illustrated in the drawings, is constructed generally in accordance with the teachings of U.S. Pat. No. 4,213,458 and reference may be had to that patent for information on the details of construction. Faceplate 11 includes a highly flexible patch or panel 17 formed of gas-penetrable but water resistant microporous material. Various materials having such properties are known and may be used. For example, a reinforced non-woven cellulosic material of the type sold under the Kaycel trademark by Kimberly-Clark Corporation, Neenah, Wis. may be used. Such material is not only air-pervious but is surface-coated with an ethyl vinyl acetate latex emulsion so that it is also heat sealable. A porous, expanded, high density polyethylene or polypropylene film of the type marketed under the designation Delnet by Hercules Incorporated, Wilmington, Del. may be included for strength and soil resistance, and other porous thermoplastic films or membranes such as Gore-Tex, a microporous polytetrafluoroethylene membrane marketed by W. L. Gore & Associates, Newark, Del., may also be employed. Effective results have been obtained using copolymer films of ethylene and vinyl acetate laminated to non-woven polyester or non-woven rayon layers. In any case, the faceplate should be highly flexible so that it will conform readily to body contours and body movements, and be coated on its back or rear side with a medical-grade pressure-sensitive adhesive so that upon removal of backing sheet or sheets 18 the microporous adhesive-coated patch or panel 17 may be secured to the patient's skin in the peristomal region.

An attaching ring or collar 19 may be secured to the front face of the microporous patch 17 by heat sealing or by any other suitable means. In the illustrated embodiment, attaching ring 19 is heat sealed to the microporous patch 17 along inner and outer concentric heat seal zones 20 and 21, respectively. The attaching ring reinforces the microporous patch 17 in the area about faceplate opening 22 and should be formed from a tough material capable of being securely joined to the patch. Thus, if the patch is formed of an ethylene vinyl acetate copolymer, the reinforcing attaching ring 19 may be formed of a material of similar composition, although not necessarily microporous. The attaching ring must also be capable of being heat sealed or otherwise securely joined, either directly or indirectly, to ring 13a of the coupling ring assembly 13. In the construction depicted in the drawings, such connection is indirect to the extent that a web 23 of thin, flexible, and resilient thermoplastic material is interposed between faceplate ring 13a and the attaching ring 19 of faceplate 11, as generally disclosed in co-owned U.S. Pat. No. 4,419,100. Specifically, the inner margin of the annular web 23 is heat sealed at 20 to the faceplate 11 and its outer margin is heat sealed at 24 to faceplate ring 13a. The web gives rise to a floating relationship between the faceplate ring 13a and faceplate 11, promoting conformity of the faceplate to a wearer's body without resistance from the coupling rings and, in general, allowing limited movement of the faceplate ring in generally axial directions with respect to the faceplate. Such limited movement allows a user to insert his (her) fingers between the ring 13a and faceplate 11 to facilitate attachment and detachment of the coupling rings without causing discomfort. The web should be formed of a heat sealable, tough, and durable material that is also capable of functioning as a fluid and odor barrier. Low density polyethylene coextruded with a coextensive layer or core of polyvinylidene chloride, known under the designation Saranex, from Dow Chemical Company, Midland, Mich., has been found suitable but other materials having similar properties are available and may be used.

The coupling ring assembly, and particularly the structural relationship between faceplate ring 13a and pouch ring 13b, is illustrated most clearly in FIG. 4. Ring 13a has an annular body portion 25 and an integral tubular neck portion 26. It will be observed that the body portion 25 is planar and, specifically, extends along a plane normal to the central axis of the coupling ring 13a. At its outer limits, the planar body portion 25 provides an annular latching shoulder 27 that is shown to be continuous although, if desired, the latching shoulder may be discontinuous or interrupted along its circumference. The shoulder is rounded in longitudinal section as shown in FIG. 4 to facilitate latching engagement with pouch ring 13b.

The neck portion 26 of ring 13b is generally frusto conical in configuration and tapers axially and forwardly away from planar body portion 25. The smooth frusto conical outer surface 26a of neck portion 26 is intended for sealing engagement with the pouch ring 13b. At its front or distal end, neck portion 26 has an annular and radially-outwardly projecting rim 28 that is preferably rounded when viewed in longitudinal section (FIG. 4).

In the embodiment of FIGS. 1–8, an outer flange 29, lying in a plane parallel with but spaced behind the plane of body portion 25, merges with the body portion behind shoulder 27 and extends radially outwardly therefrom. The planar backside of flange 29 may be heat sealed at 24 to web 23 or, if desired, may be secured directly to faceplate 11 (in which case web 23 would be omitted) as previously indicated.

The pouch coupling ring 13b is similarly provided with a body portion 30 that generally extends in a plane normal to the central axis of that ring. A generally frusto conical collar portion 31 tapers axially from the inner margin of the body portion 30, the general direction of taper of collar portion 31 being the same as that of neck portion 26. The inner surface 31a of the collar portion is provided with an annular projection 31b adjacent the free end of the collar portion, such projection defining the smallest inside diameter of the collar portion for sealingly engaging the outer surface 26a of ring 13b. The smooth rounded projection 31b essentially makes a line seal with surface 26a and to help insure sealing effectiveness the inner surface of collar portion 31 may be recessed at 31c to provide greater definition for the annular projection 31b. At its distal or free end, collar portion 31 is provided with an axially-facing annular ridge 31d that normally abuts rim 28 when the parts are assembled as shown in FIG. 4.

Along its outer perimeter, body portion 30 merges with an annular latching rib 32 which projects inwardly and axially in a direction opposite from that of collar portion 31 and which, along with the remainder of body portion 30, defines an inwardly and rearwardly facing recess 33 for detachably receiving and retaining the shoulder 27 of faceplate ring 13a. The rib 32 may be provided with rounded surfaces, as shown in FIG. 4, to facilitate latching engagement and disengagement of the two rings.

The parts are dimensioned so that when the rings are coupled together the collar portion 31 of ring 13b will be in a state of tension with annular projection 31b firmly and sealingly engaging the outer frusto conical surface 26a of neck portion 26. Since the collar portion is under tension, the restorative forces attempting to relieve such tension cause the collar portion to shift to the left, as viewed in FIG. 4. Rim 28 of ring 13a is engaged by the annular ridge 31d and functions primarily as a stop to assist in retaining projection 31b in sealing contact with surface 26a.

When the rings are coupled as shown in FIG. 4, latching zone 34 is spaced a substantial distance outwardly from sealing zone 35. The outer latching zone is not a sealing zone for purposes of effectively preventing the escape of fluids (gases as well as liquids) from within faceplate 11 and pouch 12, and in fact a tight interfit between rib 32 and shoulder 27 should be avoided since because it might interfere with completeness and ease of latching. A slight spacing between the inner surface 33 of the rib and the outer surface of the shoulder (as shown in FIG. 4) is desired.

As previously indicated, a fluid-tight sealing action occurs along inner sealing zone 35 and, specifically, between the annular projection 31b of flexible collar portion 31 and sealing surface 26a. The security of the latching action in outer zone 34, and the fact that the latching zone 34 and sealing zone 35 are separate from each other and, specifically, are spaced apart a substantial distance radially, permits the rings to be fabricated from softer and more pliable plastic materials without serious risk that deformation in use might result in unintentional disruption of the latching and/or sealing functions. While any of a variety of resilient and flexible plastic materials might be used, low density polyethylene has been found particularly effective. Other tough, pliable materials that might be suitable are polyurethane, plasticized vinyl, and thermoplastic rubbers.

The substantial radial dimensions of the body portions 25 and 30 of the two rings in relation to the axial dimensions of neck and collar portions 26 and 31 also results in a coupling assembly that is relatively flat; that is, one which does not protrude excessively from the wearer's body. While it is believed apparent that considerably dimensional variation is possible, it has been found that particularly effective performance is achieved if the radial dimension of the body portion of each ring substantially exceeds the axial length of collar portion 31 and the surface 26a sealingly engaged by that collar portion.

FIGS. 5 and 6 illustrate two ways in which the coupled rings might become temporarily deformed in use. In both views the rings are shown without associated elements (e.g., the pouch and faceplate) and the extent of deformation is somewhat exaggerated for clarity of illustration. Depending on the location of the stoma and the condition of the patient (muscle development and tone, weight condition, fat distribution, body size, etc.), bending movement of the body might cause the rings to develop the convex or outwardly (forwardly) bowed curvature of FIG. 5 or the concave or inwardly (rearwardly) bowed condition of FIG. 6. The sectional views of FIGS. 7 and 8 somewhat schematically depict the actions of the coupling rings under each of the conditions represented in FIGS. 5 and 6.

With convex deformation (FIG. 7), faceplate ring 13a is altered so that the outside diameter of annular shoulder 27, when measured vertically, increases. The upper and lower portions of the shoulder 27 tend to extend more fully in the latching recess 33 defined by rib or lip 32 to assist in retaining latching effectiveness. The deformation also tends to cause collar portion 31 to slide rearwardly along frusto conical sealing surface 26a and, because of the conical configuration of that surface, the force of sealing engagement between collar portion 31 and neck portion 26 also increases.

Under conditions of concave deformation (FIG. 8), shoulder 27 still remains seated within latching recess 32 but the collar portion 31 slides in the opposite direction along surface 26a into engagement with annular rim 28. The annular projection or bead 31b of the collar portion remains in sealing engagement with surface 26a.

Pouch ring 13b optionally may be provided with lateral ears 36 having apertures 37 so that the bag may be connected to a suitable belt or strap (not shown) or a conventional belt having a ring interposed between pouch 11 and the web 23 of faceplate 13a may be used. A tab portion 38, projecting radially outwardly from ring 13b at some point between lateral ears 36, may also be provided to assist a user in stretching or pulling a portion of the latching rib or lip 32 away from shoulder 27 for venting purposes or so that separation may be propagated in circumferential directions from that point to bring about complete detachment of the coupling rings from each other.

In the embodiment illustrated in the drawings, ring 13a is mounted on the faceplate 11 and ring 13b on bag 12. Such an arrangement is important for a number of reasons, one being that when the faceplate is secured to a patient, the neck portion 26 of ring 13a tends to protect the stoma from direct contact with collar 31 of ring 13b as the rings are coupled and uncoupled because, as shown in FIGS. 3 and 4, collar 31 seals about the outside, not the inside, of neck 26. It is to be understood, however, that under some circumstances it might possibly be advantageous to reverse the arrangement so that ring 13a would be mounted on the bag and ring 13b on the faceplate.

Figure 9:
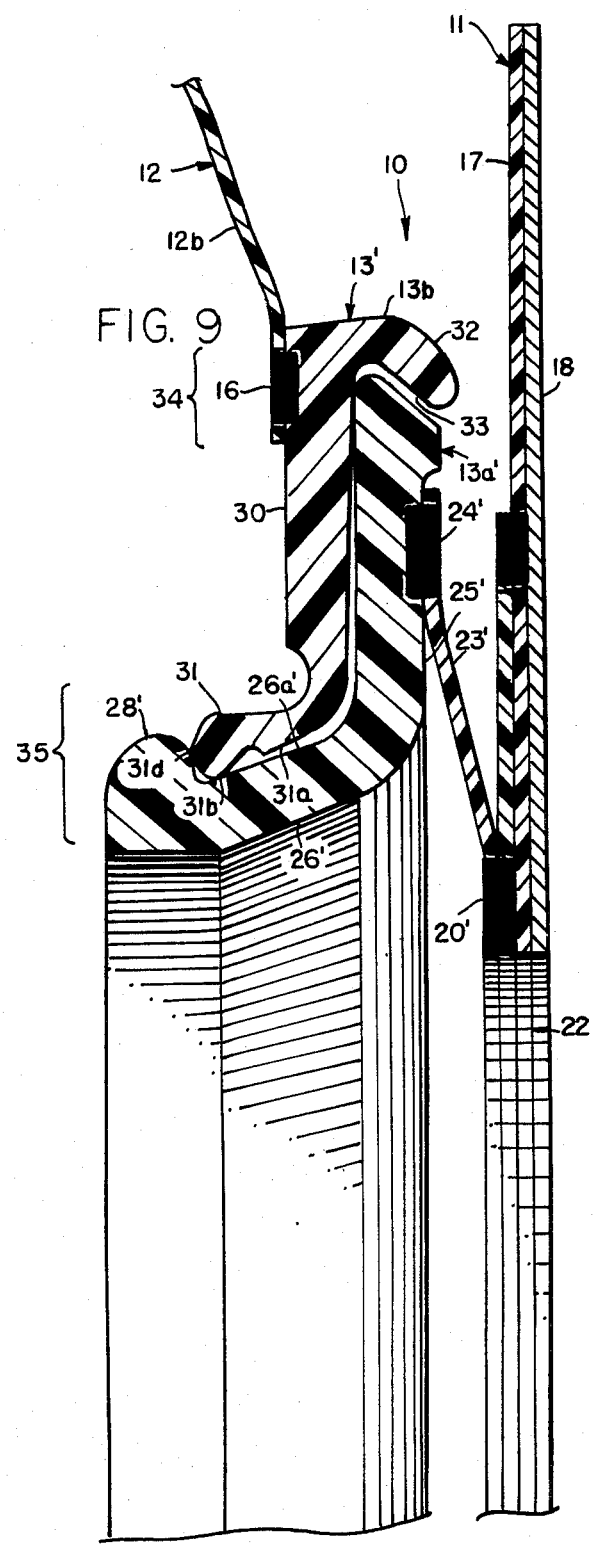
FIG. 9 is a greatly enlarged fragmentary sectional view similar to FIG. 4 but illustrating a second embodiment of this invention.

The embodiment illustrated in FIG. 9 is identical to the embodiment already described except that outer flange 29 is eliminated from faceplate ring 13a' and web 23' is reduced in size and connected along its outer margin by heat seal line 24' to the body portion 25' of the ring rather than to the outer flange 29 of the earlier form. In terms of latching and sealing structure and the functional relationship between such parts, there are no differences between the embodiment of FIG. 9 and that of FIGS. 1-8 and, therefore, the description concerning the earlier version is fully applicable to the latter.

Assuming that the latching and sealing components of the two embodiments are of equal size, the FIG. 9 version results in a coupling ring assembly of smaller outer diameter because of the elimination of outer flange 29. However, because the outer flange is omitted and because flexible web 23' is of smaller radial dimension that web 23, the "floating" action between faceplate 11 and ring 13a' is reduced. Where such reduction is acceptable from the standpoint of user comfort, convenience, and ease of operation, the embodiment of FIG. 9 is preferred because of the smaller outer dimensions of the faceplate ring 13a' and, hence, of the entire coupling ring assembly 13'.

While in the foregoing we have disclosed embodiments of the invention in considerable detail for purposes of illustration, it will be understood by those skilled in the art that many of these details may be varied without departing from the spirit and scope of the invention.

We claim:

1. A coupling for detachably connecting an ostomy faceplate to an ostomy pouch, said coupling including first and second coupling rings formed of flexible thermoplastic material; said first coupling ring having an annular body portion merging along its inner perimeter with a tubular neck portion extending axially away from said body portion; said neck portion having an outer sealing surface and having a free end terminating in an annular and radially-outwardly projecting rim; said second ring also having an annular body portion and having an inner collar portion detachably receiving said neck portion, with said collar portion extending axially away from the body portion of said second ring in generally the same direction as said neck portion and with the inside of said collar portion sealingly engaging the outer surface of said neck portion; wherein the improvement comprises said annular body portion of said first ring being generally planar and defining an annular latching shoulder extending about the outer perimeter thereof; said body portion of said second ring also being generally planar and having an annular latching rib extending about the outer periphery thereof in a generally axial direction opposite from the direction of said collar portion; said latching rib, along with the remainder of said body portion of said second ring, defining a latching recess detachably receiving and retaining the shoulder of said first ring.

2. The coupling of claim 1 in which said neck portion of said first ring is frusto conical with a taper extending away from the body portion of said first ring.

3. The coupling of claim 2 in which said collar portion is generally frusto conical with a taper extending away from the body portion of said second ring.

4. The coupling of claim 3 in which said collar portion has an axial length less than the outer sealing surface of said neck portion and is capable of limited axial sliding movement between said rim and the body portion of said first ring.

5. The coupling of claim 4 in which said collar portion is in a state of tension when said neck portion is received therein.

6. The coupling of claims 1 or 5 in which said coupling also includes a faceplate; and mean connecting said faceplate to said first ring adjacent the outer periphery thereof.

7. The coupling of claim 6 in which said means comprises an annular web having concentric inner and outer edges; said inner edge being secured to said faceplate and said outer edge being secured to said first ring.

8. The coupling of claim 6 in which said annular body portion of said second ring is connected to a collection pouch.

9. The coupling of claim 1 in which said collar portion is provided adjacent the free end thereof with an annular projection defining an opening having the smallest inside diameter of said collar portion; said annular projection forcefully and sealingly engaging the outer surface of said neck portion when said rings are assembled.

10. The coupling of claim 9 in which said annular projection is smoothly rounded when viewed in longitudinal section.

11. The coupling of claim 10 in which said collar portion is provided with an annular recess about the inner surface thereof between said projection and said body portion of said second ring.

12. A coupling for detachably connecting an ostomy faceplate to an ostomy pouch; said coupling including first and second coupling rings formed of flexible and resilient thermoplastic material; said first coupling ring having an annular body portion merging along its inner perimeter with a tubular neck portion extending axially away from said body portion; said neck portion having an outer sealing surface and having a free end terminating in an annular and radially-outwardly projecting rim; said second ring also having an annular body portion and having an inner collar portion detachably receiving said neck portion, with said collar portion extending axially away from the body portion of said second ring in generally the same direction as said neck portion, and with the inner surface of said collar portion sealingly engaging said outer sealing surface of said neck portion; wherein the improvement comprises said annular body portions of said first and second rings being generally planar and extending along substantially parallel planes, with each of said body portions having a radial dimension greater than the axial dimension of said outer sealing surface of said neck portion; said body portion of said first ring defining an annular latching shoulder extending about the outer perimeter thereof; said body portion of said second ring providing an annular latching rib extending inwardly and axially from the outer periphery thereof, with the axial direction of said rib being opposite from the axial direction of said collar portion; said latching rib, and the body portion of said second ring, defining a latching recess detachably receiving and retaining the shoulder of said first ring.

13. The coupling of claim 12 in which said neck portion and said collar portion are generally frusto conical in configuration, each having a taper extending away from the body portions of the respective rings.

14. The coupling of claims 12 or 13 in which said collar portion of said second ring is in a state of tension when said neck portion is received therein.

15. The coupling of claim 14 in which said collar portion has an axial length less than that of the outer sealing surface of said neck portion.

16. The coupling of claim 14 in which said coupling also includes a faceplate; and means connecting said faceplate to said first ring adjacent the outer periphery thereof.

17. The coupling of claim 16 in which said means comprises a flexible web having concentric edges; one of said edges being secured to said faceplate and the other of said edges being secured to said first ring.

18. The coupling of claim 16 in which said annular body portion of said second ring is connected to an ostomy pouch.

19. The coupling of claim 12 in which said collar portion is provided adjacent the free end thereof with an annular projection defining an opening having the smallest inside diameter of said collar portion; said annular projection forcefully and sealingly engaging the outer surface of said neck portion when said rings are assembled.

20. The coupling of claim 19 in which said annular projection is smoothly rounded when viewed in longitudinal section.

21. The coupling of claim 20 in which said collar portion is provided with an annular recess about the inner surface thereof between said projection and said body portion of said second ring.

* * * * *